United States Patent
Heinrich et al.

(10) Patent No.: US 10,328,283 B2
(45) Date of Patent: Jun. 25, 2019

(54) METHOD AND APPARATUS FOR DETERMINING OR PREDICTING THE POSITION OF A TARGET

(71) Applicant: Brainlab AG, Munich (DE)

(72) Inventors: Steffen Heinrich, Schwaben (DE); Kajetan Berlinger, Munich (DE); Miloš Marić, Munich (DE); Christian Spika, Poing (DE)

(73) Assignee: Brainlab AG, Munich (DE)

( * ) Notice: Subject to any disclaimer, the term of this patent is extended or adjusted under 35 U.S.C. 154(b) by 25 days.

(21) Appl. No.: 15/544,941

(22) PCT Filed: Nov. 17, 2016

(86) PCT No.: PCT/EP2016/077997
§ 371 (c)(1),
(2) Date: Jul. 20, 2017

(87) PCT Pub. No.: WO2017/093034
PCT Pub. Date: Jun. 8, 2017

(65) Prior Publication Data
US 2017/0368369 A1    Dec. 28, 2017

(30) Foreign Application Priority Data
Dec. 1, 2015  (WO) ............... PCT/EP2015/078187

(51) Int. Cl.
*A61N 5/10*    (2006.01)
*G06T 7/246*   (2017.01)
(Continued)

(52) U.S. Cl.
CPC ............ *A61N 5/1049* (2013.01); *A61B 6/022* (2013.01); *A61B 6/12* (2013.01); *A61B 6/5264* (2013.01);
(Continued)

(58) Field of Classification Search
CPC .......... A61N 2005/1061; A61N 5/1049; G06T 2207/30241; G06T 7/285; G06T 17/00;
(Continued)

(56) References Cited

U.S. PATENT DOCUMENTS 6,144,875 A    11/2000  Schweikard et al.
6,501,981 B1   12/2002  Schweikard et al.
(Continued)

FOREIGN PATENT DOCUMENTS

WO     20090015767    2/2009

OTHER PUBLICATIONS

International Search Report and Written Opinion from corresponding International Application No. PCT/EP2016/077997, dated Feb. 2, 2017, pp. 1-13.
(Continued)

*Primary Examiner* — Kenny A Cese
(74) *Attorney, Agent, or Firm* — Tucker Ellis LLP

(57) ABSTRACT

A data processing method for determining the position of a target, comprising the steps performed by a computer: a) acquiring a target movement model specifying a movement cycle of the target; b) acquiring a target position signal representing a view of the target from a single direction and/or provided by a single imager; c) determining, based on the acquired target position signal and the target movement model, the position of the target.

19 Claims, 5 Drawing Sheets

(51) Int. Cl.
  *G06T 7/73* (2017.01)
  *A61B 6/02* (2006.01)
  *A61B 6/12* (2006.01)
  *A61B 6/00* (2006.01)
(52) U.S. Cl.
  CPC .............. *G06T 7/246* (2017.01); *G06T 7/251* (2017.01); *G06T 7/75* (2017.01); *A61N 2005/1061* (2013.01); *G06T 2207/10012* (2013.01); *G06T 2207/10048* (2013.01); *G06T 2207/10116* (2013.01); *G06T 2207/30004* (2013.01); *G06T 2207/30204* (2013.01)
(58) Field of Classification Search
  CPC .. G06T 7/55; G06T 7/251; G06T 7/75; G06T 7/246; G06T 2207/30204; G06T 2207/10012; A61B 6/12; A61B 6/5264; A61B 6/022
  See application file for complete search history.

(56) References Cited

U.S. PATENT DOCUMENTS

| | | | |
|---|---|---|---|
| 8,391,955 B2 | 3/2013 | Erbel et al. | |
| 8,597,211 B2 | 12/2013 | Berlinger | |
| 8,634,898 B2 | 1/2014 | Adler et al. | |
| 2001/0043738 A1* | 11/2001 | Sawhney | G01S 5/163 382/154 |
| 2008/0137940 A1* | 6/2008 | Kakinami | G01C 11/00 382/154 |
| 2010/0067739 A1* | 3/2010 | Mostafavi | G06T 7/285 382/103 |
| 2010/0125195 A1 | 5/2010 | Berlinger et al. | |
| 2012/0051515 A1 | 3/2012 | Brown | |
| 2012/0123250 A1 | 5/2012 | Pang et al. | |
| 2014/0046172 A1 | 2/2014 | Kim et al. | |
| 2014/0362193 A1* | 12/2014 | Kanetake | G01S 1/00 348/50 |

OTHER PUBLICATIONS

Poels, Kenneth, et al., "A comparison of two clinical correlation models used for real-time tumor tracking of semi-periodic motion: A focus on geometrical accuracy in lung and liver cancer patients", Radiotherapy and Oncology, (2015), p. 1-6.

Wolfelschneider, Jens, et al., "Quantification of an External Motion Surrogate for Quality Assurance in Lung Cancer Radiation Therapy", Hindawi Publishing Corporation, BioMed Research International, (2014), vol. 2014, Article ID 595430, pp. 1-8.

* cited by examiner

METHOD AND APPARATUS FOR DETERMINING OR PREDICTING THE POSITION OF A TARGET

RELATED APPLICATION DATA

This application is a national phase application of International Application No. PCT/EP2016/077997 filed Nov. 17, 2016, published in the English language, which claims benefit of International Application No. PCT/EP2015/078187 filed Dec. 1, 2015.

FIELD OF THE INVENTION

The present invention is directed to the determination of the position or a positional information of a target, such as a structure moving within a body, which determined position can for example be used to control irradiation of the target. The determined position can be used to update a correlation model correlating a surrogate signal, such as an IR marker signal with the position of the target.

BACKGROUND OF THE INVENTION

During the performance of a dynamic tracking or gated patient treatment in the field of radio therapy, a surrogate signal, such as a breathing signal, used to determine or correlate and extrapolate the target motion internal of the patient may change as the patient rests on the couch. A change may result from a repeated vital motion, such as breathing or heartbeat, but may also change in a more permanent manner, i.e. the change is not a repeated movement. This later change is primarily manifested as a shift called baseline shift. If a correlation model (or target-marker-model) is not altered or updated in order to adapt to this later change, the irradiation will likely miss the target. The change of a surrogate signal can take place while a patient is being treated.

In systems like Vero (of Brainlab) both X-ray imaging sources always have clear lines of sight on the target and thus, the correlation model can be easily updated using the 3D target coordinates obtained from stereoscopically taken X-ray images. The external markers can always (or most times) be detected. However, if a different system is used having a structure where one out of two X-ray imaging sources has no clear line of sight and is e.g. blocked, for example by a gantry, such as the ExacTrac (of Brainlab), the calculation of the correct 3D coordinates was impossible.

PRIOR ART

U.S. Pat. Nos. 6,144,875 A and 6,501,981 B1 disclose an apparatus and method for performing treatment on an internal target region while compensating for breathing and other motion of the patient in which the apparatus comprises a first imaging device for periodically generating positional data about the internal target region and a second imaging device for continuously generating positional data about one or more external markers adapted to be attached to the patient's body or any external sensor such as a device for measuring air flow. The apparatus further comprises a processor that receives the positional data about the internal target region and the external markers in order to generate a correspondence between the position of the internal target region and the external markers and a treatment device that directs the treatment towards the position of the target region of the patient based on the positional data of the external markers.

U.S. Pat. No. 8,634,898 B2 discloses a method of compensating for breathing and other motions of a patient during treatment including periodically generating internal positional data about an internal target region. The method further includes continuously generating external positional data about external motion of the patient's body using an external sensor and generating a correlation model between the position of the internal target region and the external sensor using the external positional data of the external sensor and the internal positional data of the internal target region. The method further includes predicting the position of the internal target region at some later time based on the correlation model.

U.S. Pat. No. 8,391,955 B2 discloses a method for determining the position of an object moving within a body, wherein the body is connected to markers, a movement signal is determined based on the measured movement of the markers, images are taken from the object using a camera or detector, wherein the camera or detector is moved with respect to the object, it is determined from which direction or range of angles or segment the most images corresponding to a predefined cycle of the movement signal are taken, and using at least some or all of the images of the segment containing the most images for a specified movement cycle, an image of the object is reconstructed.

U.S. Pat. No. 8,597,211 B2 discloses a method for determining an indicator body part subject to vital movement that is not to be irradiated and that serves as an indicator of the change in position of a body part subject to vital movement that is to be irradiated, in particular a tumor in an anatomical body. The method can further include determining an indicator trajectory that describes the vital movement of the indicator body part.

The Article "Quantification of an External Motion Surrogate for Quality Assurance in Lung Cancer Radiation Therapy", BioMed Research International, Vol. 2014 Article ID 595430 concerns the validation of the stability of the end exhale position in deep expiration breath hold (DEBH) technique for quality assurance in stereotactic lung tumor radiation therapy.

The Article "A comparison of two clinical correlation models used for real-time tumor tracking of semi-periodic motion: A focus on geometrical accuracy in lung and liver cancer patients", Radiotherapy and Oncology, 2015, June; 115(3): 419-424 concerns a head-to-head comparison of two clinical correlation models with a focus on geometrical accuracy for internal tumor motion estimation during real-time tumor tracking (RTTT).

Definitions

Target

A target is an entity, structure or organ or generally a body part and can be determined to be treated, e.g. by being irradiated with a radiation beam (radiotherapy). The target can be within the body and can for example be pathogenic tissue, such as a tumor. The target can in general be any structure and can be e.g. a neighbouring entitiy or structure to another entity or structure to be treated. The position of the target can change relative to the body (e.g. the target can move within the body, although the overall position of the body may or does not change in the same manner), e.g. due to vital movement, such as a breathing or respiratory motion, or due to a more permanent or temporarily unidirectional movement, such as sagging.

In most cases the target's position follows repeatedly a determinable or definable cycle, for example when the target moves due to a respiratory motion, probably combined with or overlaid by the mentioned unidirectional movement.

Target-Surrogate-Model/Correlation Model

A target-surrogate-model, such as e.g. a target-marker-model, specifies or defines the spatial relation or more general a correlation between the target and one or more surrogate elements, e.g. markers being, e.g. part of the patient, such as a landmark, or being attached to the patient, such as for example external IR markers.

A surrogate element can for example be a surface or surface structure, which is tracked, or a specific or distinct point which can be detected, such as e.g. by a thermo camera or range camera, such as a stereoscopic or 3D camera. The detection can be the detection of a spatial or 3D position of the respective surrogate element(s). The surrogate element can be detected by a surrogate element detector, such as the mentioned camera(s), to generate a surrogate signal which can indicate the position and/or state and/or moving behaviour, such as the moving direction and/or moving speed, of a surrogate element. The surrogate signal may be a signal of a single camera delivering for example a two-dimensional picture or series of pictures which by itself may not be sufficient to determine the 3D position of the surrogate element, but which delivers at least some positional information or a positional constrained concerning the possible position or possible positions of the surrogate element.

The term "marker" as used within this application should be understood as meaning or covering anything or any surrogate element which is able to deliver a positional and/or movement information when detected by an appropriate detecting means, such as a marker detected by a navigation system.

Likewise, the term "target-marker-model" or "correlation-model" is to be understood as not only referring to a marker, such as an IR-reflecting marker, but to any target-surrogate-model.

The position of the target can be determined using two 2D x-ray images of the target taken from different directions to uniquely determine the 3D position of the target. The position of the imagers being for example known. The 3D position of the target may be determined by back projecting and intersecting the target images of the target imagers.

The position of the marker(s) can e.g. be determined using a navigation system in case the markers are markers externally connected to the body, e.g. IR reflecting markers.

The correlation between the position of the target and the position of the marker(s) can be determined and can be saved as being (part of) the target-marker-model or correlation model.

A correlation model can for example specify the correlation between an external breathing curve, such as a chest motion in anterior-posterior-direction, and an internal target trajectory, such as for example a diaphragm motion in inferior-superior direction or lung motion.

The target-surrogate-model can be updated in case there is a change in the spatial relationship or correlation between the target and one or more of the surrogate elements or markers. In case the target is not an object to be treated but is located in a specific relationship relative to the object to be treated, a further model, such as a object-target-model, can be built specifying the relationship between the target and the object to be treated, which model can be set up and can be updated in the same manner as described herein for the target-surrogate-model or target-marker-model. This additional model can be used when treating the object, wherein the treatment of the object requires knowledge on the positional information of the object. The position of the object can then for example be determined by using both, the target-surrogate-model and the object-target-model.

Target Movement Model/Surrogate Movement Model

A target movement model can specify the movement of a target being e.g. a specification or line, such as a cycle or a loop and can be used to determine, where the target's position might be at a future time t.

A surrogate movement model can specify the movement of a surrogate element, e.g. a marker.

The update of the target movement model can be a full update e.g. establishing a new target movement model in total, or can be a partial update, e.g. updating or modifying only a section of a prior known target movement model.

The target movement model can be built e.g. by considering the target's movement over a specific time and forming an average target movement path. A target movement model can e.g. specify a movement line (straight and/or curved) of a target and can e.g. specify in addition information on the target's (average) position-dependent velocity.

Thus, it is e.g. possible to determine the time difference t2−t1 specifying the time the target requires to move from a first known position (being there at t1) to a second known position (being there at t2).

In addition, a target movement model containing time and/or velocity information can be used to predict the target's position at a specific time t.

All above statements referring to the target movement model do also apply to the surrogate movement model.

The target movement model can have parts or sections associated with one or more specific phases, such as "inhale" or "exhale".

Surrogate Signal

A surrogate signal can be a signal which can be acquired or tracked and which is correlated with the current position of a target within a body. E.g. a breathing signal can be used as a surrogate signal for determining the breathing cycle. For example the position of one or more markers, such as IR markers, externally attached to a body, can be used as a surrogate signal. The position of a (moving) target within a body, such as e.g. a target located on or next to the lung, can be determined when for example the detailed positional relation between the surrogate signal, which can be correlated e.g. with breathing cycles(s), and the target position(s) is known.

Baseline Shift

The spatial relation or correlation between the target and the surrogate signal, being e.g. correlated with one or more markers (target-marker-model or correlation model), may change over time. This can result e.g. from the target's position or a target's trajectory or moving cycle not changing within the body (except for e.g. a vital movement), but the marker(s) position changing. This can for example occur when a patient rests on a table and markers being connected or fixed to the skin of the patient shift due to sagging of the patient's tissue. As a consequence, the target-marker-model or correlation model (relation target position to marker(s)) has to change in order to correctly determine the target's position based on a detected marker position.

Position Prediction

The future position of a moving target can for example be predicted by determining a surrogate signal, predicting the change or future information of the surrogate signal, such as predicting the position a marker will have a the future time t, e.g. using the surrogate movement model, and using the target-surrogate-model and/or the target-marker-model to determine or calculate the future position of the target at time t.

In addition or alternatively, the position of a moving target can be determined by determining the present position of the target, such as determining the position being based on the target-surrogate-model, and predicting the target position based on a prior determined target movement model.

In addition or alternatively, the future position of a moving target at a predetermined time (e.g. 50 msec in the future) can be predicted using the following information:
- the position of the target at a predetermined time (measured or calculated)
- knowledge of the movement behaviour of the target (for example from a model or prior measurements and/or general knowledge), such as a movement cycle (e.g. the time needed for performing a cycle and the velocity distribution of the target over the cycle being known) or known trajectory of the target.

The predicted position at time t1 is e.g. the position at time t0 plus the movement along the (straight and/or curved) trajectory as e.g. defined by a target movement model during the time interval between t0 and t1.

Prediction Model

A prediction model contains knowledge and/or contains or can receive and evaluate information to predict e.g. by calculation the position of a target at a specific time in the future.
- Knowledge incorporated in the prediction model can be:
- Knowledge on the general movement (such as a movement cycle) of the target (e.g. due to breathing motion), e.g. based on general (e.g. anatomical or medical) knowledge
- Knowledge on the specific movement (such as a movement cycle) of the target (e.g. due to breathing motion), e.g. based on a (number of) prior measurement(s)
- Information incorporated in or fed into the prediction model can be:
- Information on a current measured and/or calculated position of the target
- Information on a current measured position of one or more surrogate signals or marker(s)
- Information on the target (e.g. size and shape)
- Target-marker-model/correlation model
- Baseline shift (measured or estimated)

Acquiring Data

The expression "acquiring" for example encompasses (within the framework of a computer implemented method) the scenario in which the data are determined by the computer implemented method or program. Determining data for example encompasses measuring physical quantities and transforming the measured values into data, for example digital data, and/or computing the data by means of a computer and for example within the framework of the method in accordance with the invention. The meaning of "acquiring data" also for example encompasses the scenario in which the data are received or retrieved by the computer implemented method or program, for example from another program, a previous method step or a data storage medium, for example for further processing by the computer implemented method or program. The expression "acquiring data" can therefore also for example mean waiting to receive data and/or receiving the data. The received data can for example be inputted via an interface. The expression "acquiring data" can also mean that the computer implemented method or program performs steps in order to (actively) receive or retrieve the data from a data source, for instance a data storage medium (such as for example a ROM, RAM, database, hard drive, etc.), or via the interface (for instance, from another computer or a network). The data acquired by the disclosed method or device, respectively, may be acquired from a database located in a data storage device which is operably to a computer for data transfer between the database and the computer, for example from the database to the computer. The computer acquires the data for use as an input for steps of determining data. The determined data can be output again to the same or another database to be stored for later use. The database or database used for implementing the disclosed method can be located on network data storage device or a network server (for example, a cloud data storage device or a cloud server) or a local data storage device (such as a mass storage device operably connected to at least one computer executing the disclosed method). The data can be made "ready for use" by performing an additional step before the acquiring step. In accordance with this additional step, the data are generated in order to be acquired. The data are for example detected or captured (for example by an analytical device). Alternatively or additionally, the data are inputted in accordance with the additional step, for instance via interfaces. The data generated can for example be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, for example determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

Computer Implemented Method

The method in accordance with the invention is for example a computer implemented method. For example, all the steps or merely some of the steps (i.e. less than the total number of steps) of the method in accordance with the invention can be executed by a computer (for example, at least one computer). An embodiment of the computer implemented method is a use of the computer for performing a data processing method. An embodiment of the computer implemented method is a method concerning the operation of the computer such that the computer is operated to perform one, more or all steps of the method.

The computer for example comprises at least one processor and for example at least one memory in order to (technically) process the data, for example electronically and/or optically. The processor being for example made of a substance or composition which is a semiconductor, for example at least partly n- and/or p-doped semiconductor, for example at least one of II-, III-, IV-, V-, VI-semiconductor material, for example (doped) silicon and/or gallium arsenide. The calculating steps described are for example performed by a computer. Determining steps or calculating steps are for example steps of determining data within the framework of the technical method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term "cloud computer" includes a cloud computer system which for example comprises a system of at least one cloud computer and for example a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing imaging methods), wherein the technical signals are for example electrical or optical signals. The technical signals for example represent the data received or outputted by the computer. The computer is preferably operatively coupled to a display device which allows information outputted by the computer to be displayed, for example to a user. One example of a display device is an augmented reality device (also referred to as augmented reality glasses) which can be used as "goggles" for navigating. A specific example of such augmented reality glasses is Google Glass (a trademark of Google, Inc.). An augmented reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. The monitor may also be the monitor of a portable, for example handheld, device such as a smart phone or personal digital assistant or digital media player.

Registering

The n-dimensional image of a body is registered when the spatial location of each point of an actual object within a space, for example a body part in an operating theatre, is assigned an image data point of an image (CT, MR, etc.) stored in a navigation system.

Computer Program

The method of the invention can be performed by a computer program. Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

Marker

It is the function of a marker to be detected by a marker detection device (for example, a camera or an ultrasound receiver or analytical devices such as CT or MRI devices) in such a way that its spatial position (i.e. its spatial location and/or alignment) can be ascertained. The detection device is for example part of a navigation system. The markers can be active markers. An active marker can for example emit electromagnetic radiation and/or waves which can be in the infrared, visible and/or ultraviolet spectral range. A marker can also however be passive, i.e. can for example reflect electromagnetic radiation in the infrared, visible and/or ultraviolet spectral range or can block x-ray radiation. To this end, the marker can be provided with a surface which has corresponding reflective properties or can be made of metal in order to block the x-ray radiation. It is also possible for a marker to reflect and/or emit electromagnetic radiation and/or waves in the radio frequency range or at ultrasound wavelengths. A marker preferably has a spherical and/or spheroid shape and can therefore be referred to as a marker sphere; markers can however also exhibit a cornered, for example cubic, shape.

Navigation System

The present invention may involve or use a navigation system. This navigation system preferably comprises a computer for processing the data provided in accordance with the computer implemented method as described in any one of the embodiments described herein. The navigation system preferably comprises a detection device for detecting the position of detection points which represent the main points and auxiliary points, in order to generate detection signals and to supply the generated detection signals to the computer, such that the computer can determine the absolute main point data and absolute auxiliary point data on the basis of the detection signals received. A detection point is for example a point on the surface of the anatomical structure which is detected, for example by a pointer. In this way, the absolute point data can be provided to the computer. The navigation system also preferably comprises a user interface for receiving the calculation results from the computer (for example, the position of the main plane, the position of the auxiliary plane and/or the position of the standard plane). The user interface provides the received data to the user as information. Examples of a user interface include a display device such as a monitor, or a loudspeaker. The user interface can use any kind of indication signal (for example a visual signal, an audio signal and/or a vibration signal). One example of a display device is an augmented reality device (also referred to as augmented reality glasses) which can be used as so-called "goggles" for navigating. A specific example of such augmented reality glasses is Google Glass (a trademark of Google, Inc.). An augmented reality device can be used both to input information into the computer of the navigation system by user interaction and to display information outputted by the computer.

A navigation system, such as a surgical navigation system, is understood to mean a system which can comprise: at least one marker device; a transmitter which emits electromagnetic waves and/or radiation and/or ultrasound waves; a receiver which receives electromagnetic waves and/or radiation and/or ultrasound waves; and an electronic data processing device which is connected to the receiver and/or the transmitter, wherein the data processing device (for example, a computer) for example comprises a processor (CPU) and a working memory and advantageously an indicating device for issuing an indication signal (for example, a visual indicating device such as a monitor and/or an audio indicating device such as a loudspeaker and/or a tactile indicating device such as a vibrator) and a permanent data memory, wherein the data processing device processes navigation data forwarded to it by the receiver and can advantageously output guidance information to a user via the indicating device. The navigation data can be stored in the permanent data memory and for example compared with data stored in said memory beforehand.

Landmarks

A landmark is a defined element of an anatomical body part which is always identical or recurs with a high degree of similarity in the same anatomical body part of multiple patients. Typical landmarks are for example the epicondyles of a femoral bone or the tips of the transverse processes and/or dorsal process of a vertebra. The points (main points or auxiliary points) can represent such landmarks. A landmark which lies on (for example on the surface of) a characteristic anatomical structure of the body part can also represent said structure. The landmark can represent the anatomical structure as a whole or only a point or part of it. A landmark can also for example lie on the anatomical structure, which is for example a prominent structure. An example of such an anatomical structure is the posterior aspect of the iliac crest. Another example of a landmark is one defined by the rim of the acetabulum, for instance by the centre of said rim. In another example, a landmark represents the bottom or deepest point of an acetabulum, which is derived from a multitude of detection points. Thus, one landmark can for example represent a multitude of detection points. As mentioned above, a landmark can represent an anatomical characteristic which is defined on the basis of a characteristic structure of the body part. Additionally, a landmark can also represent an anatomical characteristic defined by a relative movement of two body parts, such as the rotational centre of the femur when moved relative to the acetabulum.

Referencing

Determining the position is referred to as referencing if it implies informing a navigation system of said position in a reference system of the navigation system.

Treatment Beam

The present invention may be used to control a treatment beam. The treatment beam treats body parts which are to be treated and which are referred to in the following as "treatment body parts". These body parts are for example parts of a patient's body, i.e. anatomical body parts.

Imaging Methods

In the field of medicine, imaging methods (also called imaging modalities and/or medical imaging modalities) are used to generate image data (for example, two-dimensional or three-dimensional image data) of anatomical structures (such as soft tissues, bones, organs, etc.) of the human body using imagers. The term "medical imaging methods" is understood to mean (advantageously apparatus-based) imaging methods (so-called medical imaging modalities and/or radiological imaging methods) such as for instance computed tomography (CT) and cone beam computed tomography (CBCT, such as volumetric CBCT), x-ray tomography, magnetic resonance tomography (MRT or MRI), conventional x-ray, sonography and/or ultrasound examinations, and positron emission tomography. The image data thus generated is also termed "medical imaging data". Analytical devices for example are used to generate the image data in apparatus-based imaging methods. The imaging methods are for example used for medical diagnostics, to analyze the anatomical body in order to generate images which are described by the image data. The imaging methods are also for example used to detect pathological changes in the human body. However, some of the changes in the anatomical structure, such as the pathological changes in the structures (tissue), may not be detectable and for example may not be visible in the images generated by the imaging methods. A tumor represents an example of a change in an anatomical structure. If the tumor grows, it may then be said to represent an expanded anatomical structure. This expanded anatomical structure may not be detectable;

for example, only a part of the expanded anatomical structure may be detectable. Primary/high-grade brain tumors are for example usually visible on MRI scans when contrast agents are used to infiltrate the tumor. MRI scans represent an example of an imaging method. In the case of MRI scans of such brain tumors, the signal enhancement in the MRI images (due to the contrast agents infiltrating the tumor) is considered to represent the solid tumor mass. Thus, the tumor is detectable and for example discernible in the image generated by the imaging method. In addition to these tumors, referred to as "enhancing" tumors, it is thought that approximately 10% of brain tumors are not discernible on a scan and are for example not visible to a user looking at the images generated by the imaging method.

SUMMARY OF THE INVENTION

The present invention is directed to a data processing method for determining the position of a target, wherein the position might be the 3D position, such as the three-dimensional position of the target in space and/or relative to a given reference. The steps of the data processing method are performed by a computer. A target movement model is acquired specifying a movement cycle of the target. The target movement model can for example be acquired from a series of prior measurements of the target positions over a period of time, wherein for each specific time the three-dimensional position of the target is determined, for example using two radiographic images of the target taken at the same time or with a preferably known time difference or offset and from different viewing angles, so that the three-dimensional position of the target can be determined. If the target position is determined a number of times during a specific period or cycle, such as during at least one or more movements or breathing cycles, a target movement model can be built specifying the movement or a movement cycle of the target. E.g. the (average) time for moving along a full cycle or loop or curve can be determined, optionally together with the (average) movement velocity of the target along parts or sections of the cycle (velocity distribution). If the target is for example some structure or part being connected to or being at the lung, the target moves when the lung moves and if the breathing action is normal (e.g. no coughing), the target will repeatedly follow a given cycle, which can be determined once a number of target positions is acquired in order to build from the number of the acquired target positions the target movement cycle. The target movement model can for example be a movement cycle of the target in three-dimensional space, thus being for example the three-dimensional movement cycle. Alternatively, the movement cycle of the target can be a two-dimensional cycle, such as a movement within a plane. If for example the movement of the target is within a plane, the orientation of this plane in three-dimensional space can be determined. The movement cycle of the target can also be the target movement when seen or projected onto a viewing plane, such as an imaging plane. In case two imagers, such as x-ray imagers or cameras, are arranged to image the target from two different directions or viewing angles, both two-dimensional movement cycles can be combined to determine the three-dimensional movement cycle of the target.

The target movement model can in an abstract manner be seen as a positional constraint information limiting the possible positions the target can have. The target's movement model can in a simple example be a two-dimension plane, within which the target moves or moves in average, so that the target's position will never be outside this plane. Such a plane may be determined for any (organic) points performing a repeated action, such as a point on the lung moving due to breathing motion. This plane can be defined relative to a patient or relative to a reference system relative to which the patient itself does not move (only the target moves within or on the patient). Such a reference system can for example be a couch or rest on which the patient and thus the target is located. In a more elaborated way, the target movement model can be a line, such as a closed loop, specifying the possible locations the target can assume due to for example vital movements of a patient, such as a breathing motion or heartbeat.

In case a target is considered as a single point, the target movement model can specify possible locations of the target while ruling out positions the target will never assume and can for example be defined by a line, circle or plane (the plane specifying for example more positions than the target ever can assume, however, ruling out other position, i.e. positions outside the plane).

In case the target is considered to be a three-dimensional target having a arbitrary shape (such as only for explanatory purposes a sphere), the above concept of lines and/or planes specifying the target's possible positions can be maintained. In the case of a three-dimensional target, i.e. a target having an extension in the three space coordinates, such as a physical object, the term "line" or "loop" should be understood within this application as specifying a cylinder or cylindrical shape (considering e.g. the example "sphere") or as specifying a tubular area, such as e.g. a torus, specifying the possible locations the target can have. The term "plane" should be understood as specifying a three-dimensional area being delimited by parallel planes, wherein the target's position can be between these parallel planes (i.e. the two parallel planes defining between them a space which can be a possible position of a three-dimensional target, wherein the space outside this defined area, i.e. the space not being between the two parallel planes, is an area the three-dimensional target will never reach when the target moves, for example due to a vital movement).

If a "line" or "plane" as defined above for a three-dimensional object is intersected with a line of sight (back projecting a 2D image), then this line of sight (being i.e. a back projection of an imaged target) has a shape of a cylinder or tube which intersects with the plane (specified by two parallel planes), thus resulting in a three-dimensional object being within both, i.e. being within the back projection tube and being in between the parallel planes.

In case two imagers viewing the target from different viewing angles have a clear view on the target, it is well known how to determine the target's three-dimensional position based on both two-dimensional views of the images. If the position of the imagers and their viewing direction in 3D space is known, the position of the target in 3D can be determined by back projecting the target's image from each imager, wherein the target's position in 3D is at the intersection of the back projections. If only the relative position of the imagers is known, at least the position of the target relative to the imagers can be determined by intersecting the back projected images of the target.

However, in case only a single imager has a view on the target (for example because the other imager is blocked by the gantry or other means), a two-dimensional target position signal is acquired. The acquired two-dimensional information on the target position can be used as a two dimensional update signal constituting a positional constraint information on the possible location(s) of the target.

The acquired single two-dimensional update signal is taken from a single direction only. Within the above mentioned concept of back projection, the target's position cannot exactly be determined from this single two-dimensional image alone. However, an information can be determined that the target's position is on the back projecting line of the target's image in the viewing direction of the imager.

Since, as mentioned above, a target movement model was acquired prior to the state where one imager has no sight of the target, this target movement model specifying a movement cycle of the target can be used as an additional information to determine, together with the information of the imager seeing the target, the actual position of the target.

If the target movement model is for example the movement cycle of the target and if for example it was determined from a prior measurement, e.g. by using at least two imagers, that the movement cycle of the target is within a plane, and in addition the orientation or three-dimensional position of this plane in three-dimensional space and/or relative to the remaining imager is known, then the target's position can be determined by intersecting the back projection line of the target's image with the plane associated to the movement cycle of the target being known from a prior measurement or determination.

Alternatively or in addition to the above step of finding the target's position, the movement cycle of the target can be determined as a projection of the actual movement cycle of the target onto the blocked imager. The target movement model can in this case be considered as being for example a closed loop, such as an oval, on the imaging plane of the blocked imager. The epipolar line of the line of sight of the target, i.e. the projection of the line of sight of the imager seeing the target onto the imaging plane of the imager not seeing the target, can then be intersected with the target movement model, such as an oval or closed loop, in order to determine the target's actual position. The target's actual position can be determined by back projecting the obtained intersection point on the blocked imager and intersecting this back projection line with the line of sight of the non-blocked imager.

In case the target movement model is a closed loop, the epipolar line of the line of sight or back projected line of sights can probably have no, one or two intersecting points. In case the epipolar line does not intersect with the target movement model (or possible locations of the target), then probably no clear statement can be made on the target's position. Nevertheless, it is possible to determine the target's position in case there is no intersection point between the epipolar line and the target movement model, if for example the epipolar line is close to but outside of the target movement model specifying e.g. a cycle along which the target moves. In this case for example the point on the target movement model or cycle having the least distance to the epipolar line can be chosen to determine the target's position. It is possible to set a maximum distance the epipolar line can have from the target movement model to distinguish between "valid" and "invalid" points (which probably should not be used for determining the target's position). Such a maximum distance can for example be 1 mm or 5 mm or any appropriately selected distance. In addition or alternatively, the information on the history of the target's movement can be considered to determine which point on the target movement model or cycle is most likely to be the point to be considered to determine the target's position in case the epipolar line does not intersect with the target movement model. Such a target history information can be a phase information.

If there is only a single intersecting point, then this point can be used to determine the target's position. In most cases two intersecting points will be obtained. The decision which intersecting point is used can be made based on prior knowledge of the target's movement which also can be part of the target movement model using the fact that the target follows a pre-defined course according to fixed movement sections or cycles, such as "inhale" and "exhale" when a breathing motion is considered. This can also be understood as for example determining and then saving in a memory a target's movement cycle, such as a closed loop including a specification of a pre-defined direction of the target's movement (such as for example clock wise or counter-clock wise along the loop). In case two or more images are made from a moving target, it can easily be determined when knowing the target's movement direction on the target's movement loop which of probably two intersecting points is the intersecting point to be used for determining the target's position.

Thus, it is possible to determine the position of the target even if only a single imager is used or has a view of the target when considering in addition knowledge based on a target movement model which can be obtained from prior measurements and can for example be stored in a memory.

Thus, it is no longer required to provide a clear view on the target for two imagers in order to determine the position of a target, which provides the advantage that the target's position can be determined in more positions or states of a system, such as for example a patient monitoring system or a radio therapy system, than compared to the prior known devices and methods requiring the system to move back to a state where two imagers see the target.

According to an aspect, a data processing method is provided which determines an update of a three-dimensional correlation model correlating a surrogate signal with a positional three-dimensional information of a target, the target being preferably within a body. The surrogate signal can be a marker signal, such as an infrared marker signal, specifying the marker's position(s) in three-dimensional space. The markers are most times distinct from the target and can for example be positioned on the outside of the patient, e.g. on the patient's skin. The marker's position(s) can be detected by a navigation system in the known manner.

The update is based on an update signal, such as for example a two-dimensional image signal, such as an image being taken by an imager, such as an x-ray imager. The update signal can be acquired only from a single imager having a view on a target only from a single direction.

According to the invention, it is not necessary that a stereoscopic signal is provided, i.e. a signal provided by at least two imagers viewing a target from two different directions. The update signal shall include a positional information of the target, such as a target as seen from a single imager only.

Based on this update signal, the three-dimensional position of the target is determined as described above by considering in addition the prior acquired target movement model specifying the target's movement and/or being a positional constraint with respect to the target's possible positions or locations or ruling out specific target positions.

In addition, a surrogate signal is acquired, such as a signal obtained by viewing one or more markers being external to the patient by a navigation system.

The surrogate signal, such as the position of infrared marker(s), is correlated with the thus determined three-dimensional position of the target to obtain an updated correlation model.

The update of the correlation model can be a temporary update which can be used as an update of the correlation model for the time only a single imager can view the target (i.e. the other or more imagers are blocked and cannot see the target). Once it is again possible to have a stereoscopic view of the target (i.e. both or more imagers can see the target), the target's position can be determined in the known manner (i.e. by intersecting the back projections of the target's images of both imagers) and this position of the target can be correlated with the surrogate signal to obtain an updated correlation model, which can replace the temporarily updated correlation model determined while using only the signals from a single imager.

The acquired two-dimensional 2D update signal can be a signal of a single imager of a stereoscopic imaging apparatus. The positional relationship between the two imagers and/or between the imaging planes of the respective imagers is preferably known. It is possible that the invention be practised for an imaging apparatus having at least one imager (such as a monoscopic system), wherein one or more additional imagers can be present. For practising the invention, at least one imager provides an image signal containing information of the target, i.e. at least part of the target and preferably the whole target is depicted on the image plane of the respective imager.

The determination of the three-dimensional 3D position of the target can include a determination based on a prior determined dependency between the 3D position of a target and the target's projection on the imaging plane of the imager acquiring the 2D update signal. The prior determined dependency can for example be a knowledge of the target's movement line or movement part, i.e. the information on all possible locations the target can assume during a vital movement. The prior determined dependency can for example be the information in which plane or in which three-dimensional limited space the target can move. Having this a priori knowledge of the target's possible positions, which can be considered as a positional constraint information of the target being known prior to or at least at the time of imaging the target, the 3D position of the target can be determined from a 2D view of the target alone, such as from the target's image or series of images taken from an imager viewing the target from only a single direction (i.e. being no stereoscopic image).

According to an alternative version which can be practised together with the above described version, the determination of the 3D position of the target can include the determination of the epipolar line corresponding to the target's position detected by one imager, the epipolar line being on the imaging plane of a further imager, such as an obstructed or for some other reason not working or no information signal delivering imager. The intersection or intersections between the determined epipolar line and the projected target movement model specifying the target's movement (the target's possible location being projected onto the second imaging plane) is determined. The projection of a movement cycle can be part of or can be a prior acquired target movement model.

The target movement model can be acquired based on at least one of the following information:

The latest or the latest available or some of the latest available actual target detection(s) on a not used or obstructed imager, e.g. the latest possibility that a stereotactic image of the target is made which provides the possibility of exactly determining the target's position at that time. This information can for example be used to set up a target movement cycle or movement plane within which the target moves, especially when in addition to the latest target detection prior or immediate prior positions of the target are used, which enables to construct or determine at least parts or in full a target movement range or target movement cycle. It is noted that out of a series of available recent target detections one or more target detections can be used, even without using the very last.

The latest prediction of the 3D target position. The prediction can be based on the latest correlation model and the latest acquired surrogate signal. Other than described above, the 3D target position can be determined not based on the last available actual measurement, but on the latest prediction. Due to the nature of a prediction being based on a previous prediction, it is assumed that often the prediction of the 3D target position is more accurate if being based on the latest actual target detection, such as a latest stereoscopic target detection. However, if for example the latest stereoscopic target detection was made some time ago, a prediction being made on a previous prediction using the present invention may be more accurate.

The latest prediction of the target position being projected onto the obstructed imager may be used as well for establishing a target movement model.

A target movement cycle can be associated with specific phases being specific for the target's position. Such a specific phase can for example be "inhale" and "exhale", if the target is for example located in, on or near the lung. A target movement cycle can also be associated with for example the heartbeat, like "contraction" or other specific phases of an organ having some specific movement depending on the target's location being in, on or next to this organ.

The specific phases can be associated with the surrogate signal, such as detected marker position(s). For example, a relative marker position can be determined, the relative position specifying the marker's position relative to an average or mean position when considering a series of marker positions detected over time. A relative marker position can for example be "more outside" of the body, which may be associated to the specific phase "inhale" or may be "more inside" of the body, which may be associated with the specific phase "exhale". The terms "more outside" and "more inside" are to be understood as specifying a relative position of the marker when considering the marker's movement, e.g. the marker is for example permanently located outside of a body, such as e.g. on a belly, and moves together with the belly to be "more outside", if the belly is more outside, and to be "more inside", if the belly is more inside. Anyway, the marker's position relative to for example the skin to which it may be attached does not change. The specific phases can be determined or associated with the velocity or gradient of a surrogate element, wherein the direction of the movement, such as "to the inside" or "to the outside", determines the specific phase, e.g. "exhale" or "inhale".

Since it is known that for a normal breathing motion an "inhale" phase is followed by an "exhale" phase and so on, wherein both phases may have about the same length, it is possible to include an information in the target movement model specifying which of the specific phases a patient may likely have at a specific time. For example, the "inhale" and "exhale" periods are measured for building the target movement model and within the target movement model it is assumed, that a patient continues to breathe following the same breathing-scheme as was present at the time when the target's movement model was built. It is thus possible to determine that a patient may be at the specific phase "inhale" or at the specific phase "exhale" for a specific time in the future. If it is determined from a measurement that the predetermined sequence of the specific phases has changed, e. g. due to a patient coughing, then this can be indicated to a user and if it is possible to determine the then current state or current sequence of the specific phases from a recently made measurement, then this information can be used within the target movement model. The above reference due the specific phases for breathing can also be applied to other vital motions, such as heartbeat.

The information on the specific phases can be used when determining the target position. In case the target movement model, when being combined with the information taken from the update signal, provides more than one possible locations of the target (e. g. the target movement model is a movement cycle which is intersected with a line specifying possible locations of the targets based on the target's image of single imager), then a decision can be made which one of the two possible locations of the target is the correct one, if the target movement cycle (as an example of the target movement model) includes information on the specific phases. For example one half of the movement cycle is known to be correlated to the specific phase "inhale" and the other half is correlated to the specific phase "exhale". If it is known from the target's movement model that the patient is likely in for example the state of "inhale" at the time the image of the target was taken, then the correct point of the possible two locations of the target can be determined. This can also be done to perform a plausibility check, i.e. to check whether the target movement model is still correct or whether the combination of the target movement model with the update signal provides a plausible movement sequence of a patient (which may not be the case if for example only a serious of "exhale" points are determined when combining the target movement model with the update signal).

The target movement model can be determined and/or updated based on a number of update points which are preferably distributed or equally or almost equally distributed in time over the movement of the target. For example, it is advantageous to build or update a target movement model based on a number of points including "inhale" and "exhale" points, whereas a model including for example only "inhale" points may lead to inferior results. The target movement model can be built or updated using a higher number of points where there is a larger change or change rate of the target's position, such as the target making a sharp curve within a movement cycle, and can use fewer points in case there is lesser change, e.g. the target follows basically a straight or almost straight line along a specific section of the target movement model. In case it is known that the target might be treated in a specific section of the target movement model, it is advantageous to have more points or a higher density of points being distributed over its section, so the target movement model can be formed more accurately in this section.

In addition to updating a correlation model as described above, a prediction model predicting the 3D position of the target in a body can be updated as well, preferably by using the update correlation model as described above.

The prediction of a target position can for example be performed by predicting the surrogate signal and determining the target's position based on the predicted surrogate signal being input into the target-surrogate-model. Following another approach, the prediction of a target position can for example by performed by determining the movement, such as the "average" movement, of the target along the movement cycle over time. The current target position can be acquired or determined using the (updated) correlation model. The prediction (in for example 40 milliseconds) is possible by adding to the determined or acquired current position the average movement (e.g. starting from the current position plus 40 milliseconds).

A system for determining the position of a target can comprise a target movement model generator being able to acquire a target movement model specifying the movement behaviour or a movement cycle of the target. The movement cycle can be only the positional information on the target's possible positions and can in addition optionally includes time-dependent and/or velocity-dependent information specifying e.g. the velocity the target has (in average) at a specific location of the target's movement cycle. The target movement model generator may use or be connected to or may even include an imaging system, such as a stereoscopy x-ray imaging system, being able to determine the target's positions while the target performs a movement over at least one out of probably a plurality of periodic and repeated movement cycles. The target movement model generator may use or be a memory to store the target movement model. This system may further include a target position acquiring element or target position detector which can be a single imager being for example one imager of a or the stereoscopic imaging apparatus or being separate therefrom. The system may further include a determination section being connected to the target movement model generator and the target position acquiring or the target position detector and receiving information or signals from both to determine, based on the acquired target position signal and the target movement model, the position of the target.

The system may comprise the computer to perform the calculations and may comprise a memory storing the information of the target movement model.

A system for updating a correlation model correlating a surrogate signal with a positional information of a target comprises a computer or processor which can perform the method steps described above. The computer or processor can acquire the above described information or signals from one or more imagers and from a memory storing for example the target movement model and can determine the 3D position of the target based on this information.

BRIEF DESCRIPTION OF THE DRAWINGS

In the following, the invention as described with reference to the enclosed figures which represent preferred embodiments of the invention. The scope of the invention is however not limited to the specific features disclosed in the figures, which show.

DETAILED DESCRIPTION

Figure 1:
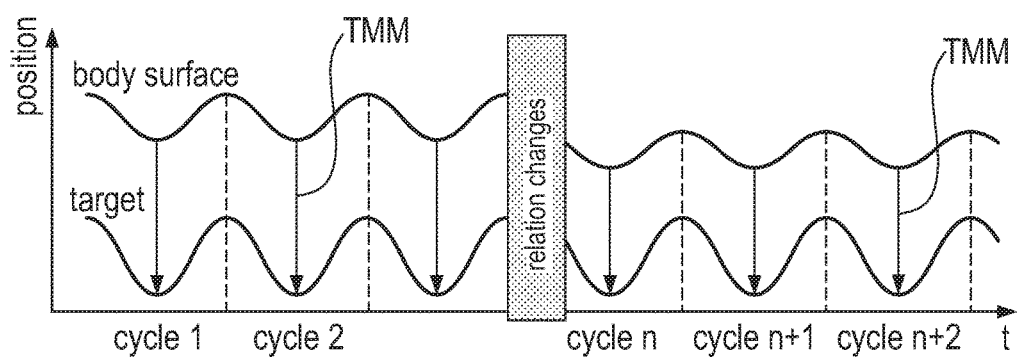
FIG. 1 a depiction of the base line shift.

FIG. 1 shows in an abstract form a positional change of a surrogate signal being an upper sinusoidal wave. The surrogate signal might be the detected positions of one or more markers being located on the body surface of a patient, the body surface moving, for example due to a breathing motion. As can be seen on the left side of FIG. 1, the surrogate signal is a periodic signal having repeated cycles 1, 2, . . . .

Below the surrogate signal there is shown as another sinusoidal signal the position of a target also moving due to a vital motion, such as a breathing motion. Same as the above surrogate signal, the below target position performs a periodic movement.

If the target's position at a specific time is correlated with the marker position or surrogate signal, then a target-marker-model TMM or in an abstract manner a correlation model can be defined specifying the relation between the detected surrogate signal (e.g. movement of the body surface) with the movement of the target. Thus, it is possible to determine a target's position based on only the surrogate signal alone, e.g. based on only the detected marker position(s). As can be seen, the relationship or distance between the surrogate signal and the target position may vary over a cycle, which variation can be included into the target-marker-model. The target-marker-model can e.g. be this stored relationship over one cycle.

However, this relation may change due to for example sagging movement of the patient lying on a couch for a longer time. If for example the body surface to which the markers are attached sags down, then the target-marker-model TMM or correlation model changes. As can be seen on the right side of FIG. 1, even after the change in relationship, it is still possible to use a surrogate signal to determine the position of the target. However, the target-marker-model or correlation model has to be adapted to the change of the relation.

Figure 2:
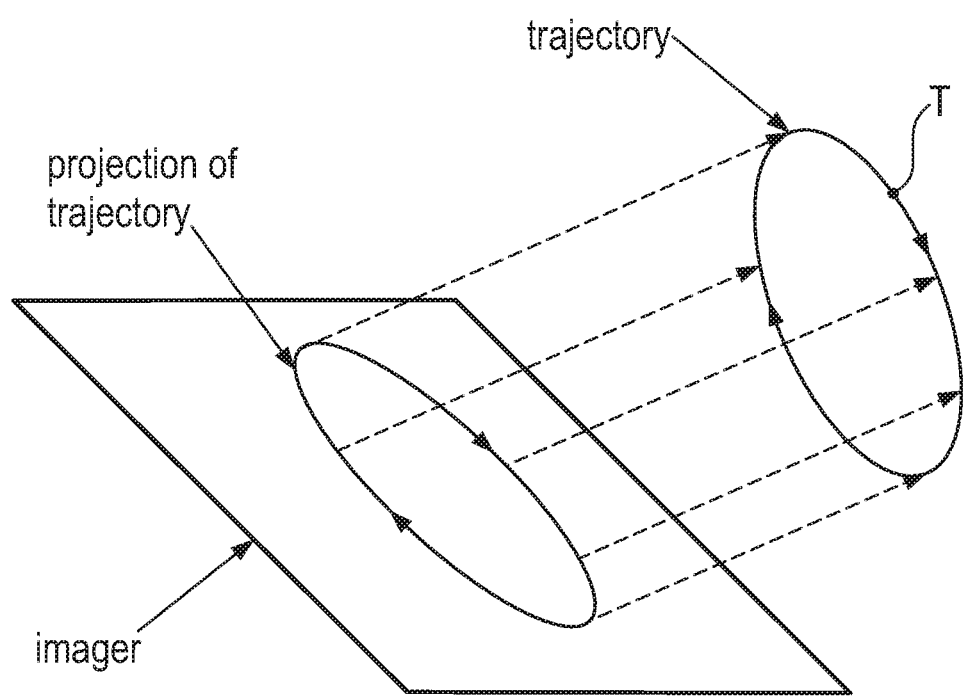
FIG. 2 the relationship between the 3D target position and its 2D projection onto an imager plane.

FIG. 2 shows a target T moving in a simplified manner along a predefined path being a circle. The movement cycle of the target T defines a trajectory drawn in a solid line.

An imager viewing the target's movement from a single specified direction has an imaging plane P. The trajectory of the target T is projected onto the imaging plane P of the imager when the target's movement is seen from the imager. The target's movement cycle being in the shown example a circle may be projected onto the imaging plane P being there an oval. The projected trajectory can itself be acquired and can for example be used as an embodiment of a target movement model. Advantageously, parts of the trajectory can be associated with specific movement cycles, such as "inhale" and "exhale". The trajectory can have a specific direction (in the shown example: clockwise) as indicated by arrows.

When the target T moving along the trajectory is imaged by a stereoscopic camera, i.e. by two cameras viewing the target from different viewing angles, the target's trajectory is projected onto each of the respective imaging planes and for every imager there can be made a target movement model as described above. If both imagers see the target, the target's position can be determined by back projection.

According to an aspect, the target movement model (for example the target trajectory line projected onto the image plane) of the obstructed imager is used in combination with the image of the imager seeing the target for determining the target's position.

A target movement model can thus for example be built by the projected trajectory of one or of both imagers.

A target movement model can for example be built during an initial stereoscopically taken movement sequence, such as an X-ray fluoro sequence, and can be updated whenever images from both imagers or both X-ray panels are simultaneously available. The update of the target movement model can be a full update e.g. establishing a new target movement model in total, or can be a partial update, e.g. updating or modifying only a section of a prior known target movement model.

For example, a series of shots can be taken at a predetermined phase, such as e.g. "fully exhale", and depending on the determined position of the target the target movement model can be modified. If for example an offset is detected in a specific phase, the whole target movement model can be updated or shifted by the detected offset.

Exemplary Solution

If coordinates of target's projection are given with $x_i$ and $y_i$, and predicted 3D target position with x', y' and z' then this model has the form:

$$f_x(x_i,y_i) \to x' \quad (1)$$

$$f_y(x_i,y_i) \to y' \quad (2)$$

$$f_z(x_i,y_i) \to z' \quad (3)$$

Dependency between 3D position and projection is modeled with linear functions whose parameters are calculated using linear regression and have the form:

$$x'=a_x x_i + b_x y_i + c_x \quad (4)$$

$$y'=a_y x_i + b_y y_i + c_y \quad (5)$$

$$z'=a_z x_i + b_z y_i + c_z \quad (6)$$

These equations can be written as:

$$\vec{t_{3D}}' = M_{3D}\vec{t_{2D}} \quad (7)$$

where $\vec{t_{3D}}' = (x',y',z')^T$ represents predicted target position, $\vec{t_{2D}} = (x_i,y_i,z_i)^T$ represents projection's position and the actual 3D model is:

$$M_{3D} = \begin{pmatrix} a_x & b_x & c_x \\ a_y & b_y & c_y \\ a_z & b_z & c_z \end{pmatrix} \quad (8)$$

According to an alternative solution, the 3D position of the target can be predicted or determined out of an image taken from a single imager (2D detection), for example being based on the principles of epipolar geometry.

Figure 3:
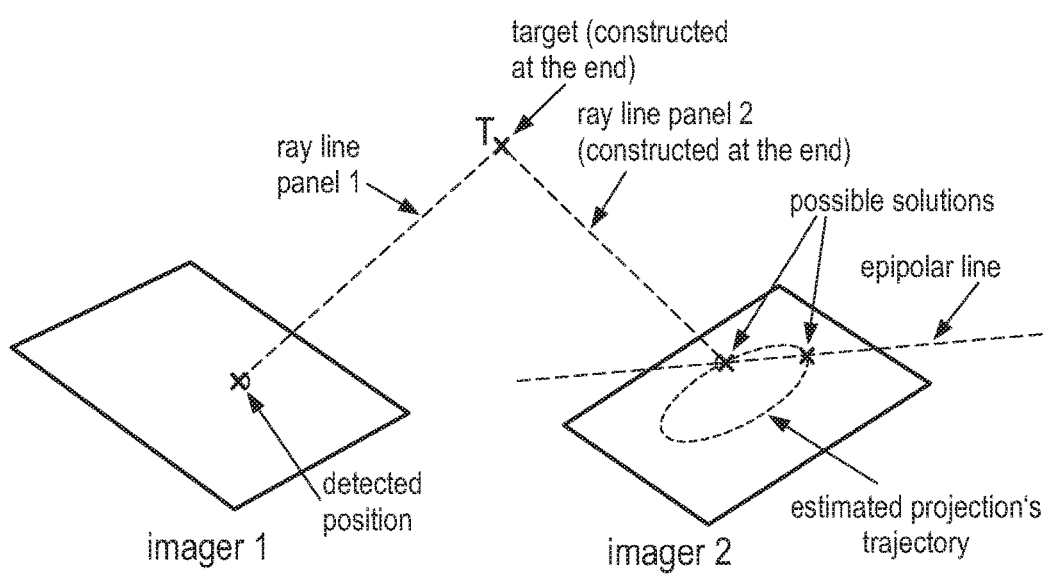
FIG. 3 a target detection based on a target movement model and a non-stereoscopic image.

This is illustrated in FIG. 3 which shows the imaging planes of two imagers, imager 1 and imager 2, which were able to both image the target when setting up the target movement model. Imager 2 is obstructed in the shown example, but from a prior measurement the estimated target's trajectory as being projected onto the imaging plane of imager 2 is shown in the dotted oval line. Imager 1 can detect a point corresponding to the position of the target T. The back projection of the detected position of target T onto the target T (i.e. the line of sight of imager 1) is projected as the epipolar line shown as a broken line onto the imaging plane of imager 2. The epipolar line can be interpreted as specifying all possible locations of target T as detected by imager 1 when projected onto the image plane of imager 2. Since from the prior measurement the target's projected trajectory is known, the epipolar line can be intersected with the target's trajectory, thus obtaining two possible solutions shown as two crosses within the imaging plane of imager 2 defining two possible locations of the target in space (which can be determined when back projecting the detected position of imager 1 and the estimated position being one of the possible solutions of imager 2, the intersection of both back projections being the position of the target). The absolute or relative position and/or orientation of the imagers being known.

In case the specific movement cycles or specific phases of the target's movement are as well known (being for example part of the target movement model), then it can be determined which one of the two possible solutions of FIG. 3 is the correct solution, thus ruling out one of the intersection points. The current breathing phase is for example known from the surrogate signal, such as from an acquired infrared marker signal.

By computing the movement phases, such as breathing phases, a plausibility check can additionally be performed to determine how "valid" the model for the obstructed imager still is.

In order to predict the 3D position of the target at any given moment the target's projection onto the X-ray panel (2D position) at the same moment can be predicted as well. For this a correlation model between a surrogate signal position and the velocity and 2D position is determined. This model can be built using a given number of most recent 2D position detections and can be updated whenever there is a new 2D detection. Furthermore, newer 2D detections can be weighted more. There can be one such model for every X-ray panel.

The couch on which a patient is located can be moved whenever a beam has to be shot from a plane other than the one in which the gantry is rotating (if the couch is in the starting position this is the axial plane). This way the angle between patient and X-ray panels changes and with it the projection, as well as the patient position in machine coordinate system, which makes existing models invalid. A straightforward solution for this problem would be to discard all previous data and make a new stereoscopic X-ray fluoro sequence, but that would extend treatment time, expose the patient to unnecessary radiation (skin dose) and could even lead to overheating.

In order to solve the couch rotation problem, a transformation matrix is used to rebuild the models, which projects 3D target positions onto X-ray panels at a new angle. This way new models can be built without a need to make new stereoscopic X-ray fluoro sequences.

Figure 4:
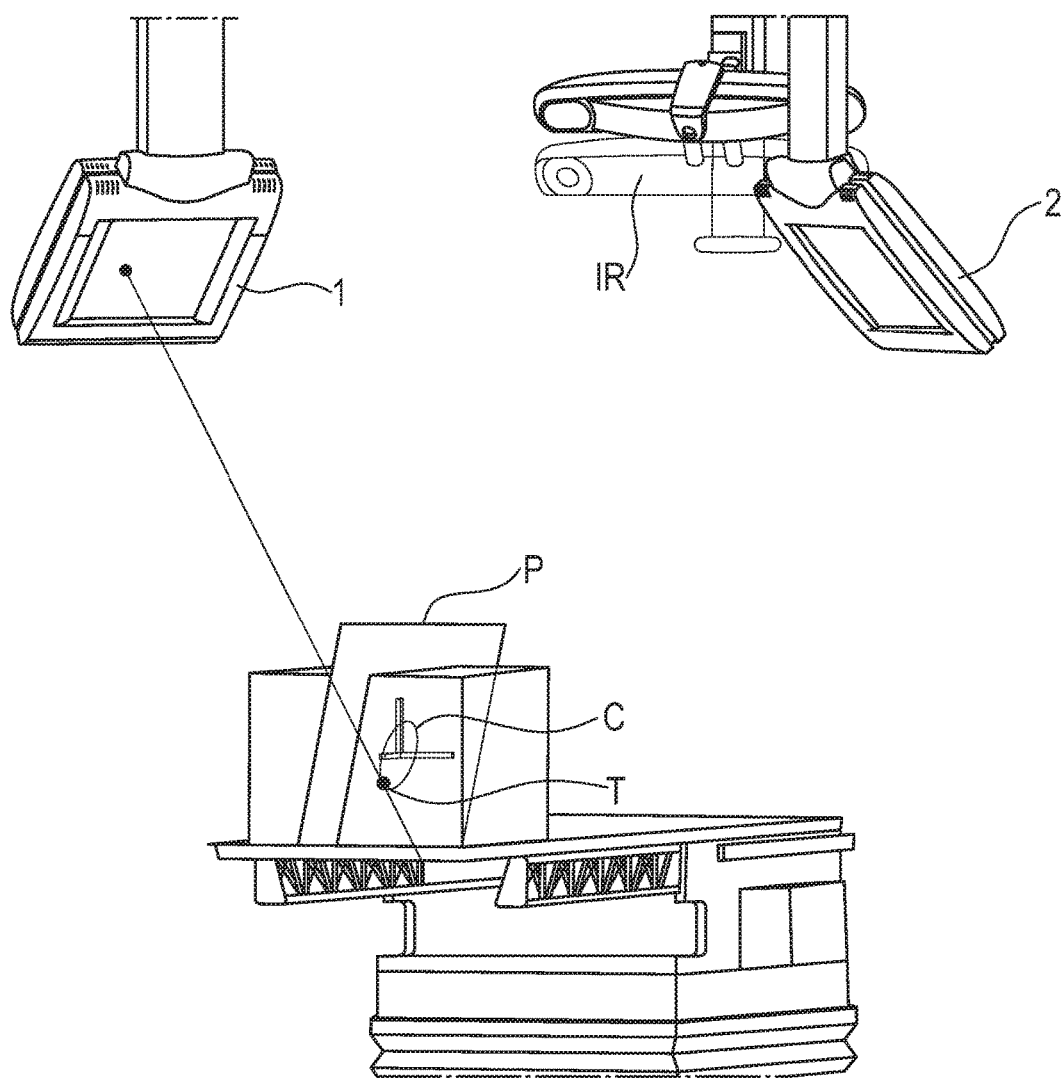
FIG. 4 a system for determining the position of a target according to a first aspect.

FIG. 4 shows an embodiment where a movement cycle or in a more simplified manner a plane is determined as a movement model. The orientation of the plane being known when determining the target movement model. FIG. 4 shows two imagers 1 and 2 being able to provide a stereoscopic X-ray view of the target T moving along movement cycle C within plane P.

In case imager 2 is blocked, the position of the target T can be determined based on only an image signal from imager 1 having a view on the target T, since the back projected image of target T being intersected with plane P and/or correlated or intersected with movement cycle C delivers the position of target T.

A stereoscopic camera IR being able to detect a surrogate signal, such as an infrared marker signal (marker is not being shown in FIG. 4) also viewing the operation scene or couch can be connected to a computer also receiving the imager signals to perform the described method.

Figure 5:
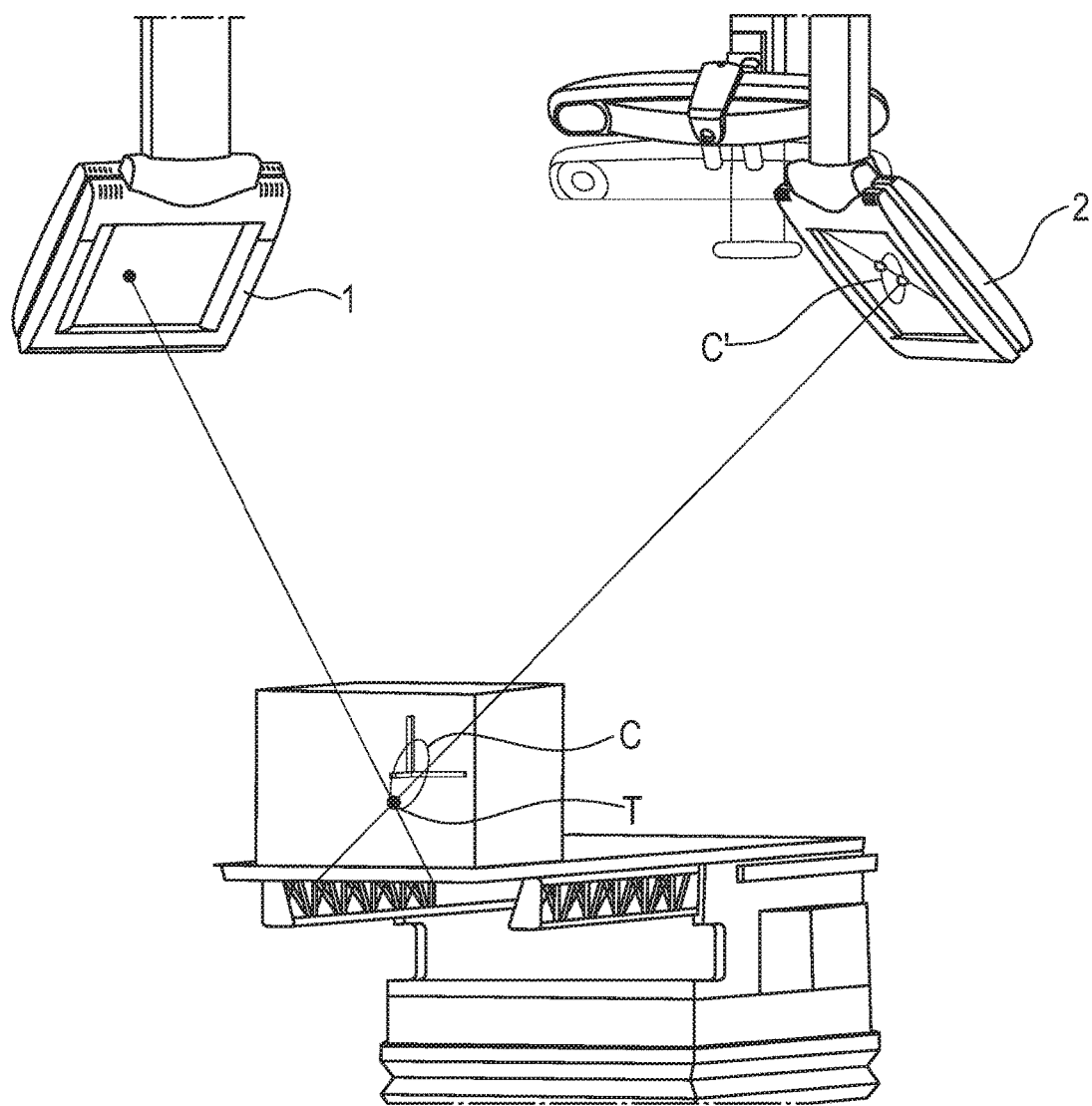
FIG. 5 a system for determining the position of a target according to a second aspect.

FIG. 5 shows a further embodiment, wherein again imager 2 does not provide a positional signal of target T due to for example being blocked by a gantry.

The target movement model is the estimated projection of the target movement cycle C onto the imaging plane of imager 2 being shown as projected trajectory C'.

The projected trajectory C' is intersected with the epipolar line of the line of sight of imager 1 and the target's position is determined as described with reference to FIG. 3.

The invention claimed is:

1. A data processing method performed by a computer for determining a three-dimensional (3D) position of a target, comprising:
   a) acquiring, using a first imager having a first imaging plane and a second imager having a second imaging plane, a target movement model specifying a movement cycle of the target, wherein the target movement model specifies at least two sections that are associated with an inhale phase and an exhale phase;
   b) acquiring, using the first imager, a two-dimensional (2D) target position signal representing a view of the target in the first imaging plane of the first imager;
   c) determining the 3D position of the target based on the 2D target position signal acquired using the first imager, and the target movement model,
   wherein the determining the 3D position of the target comprises:
      determining, based on the 2D target position signal, an epipolar line in the second image plane of the second imager corresponding to the view of the target in the first imaging plane of the first imager;
      determining at least one intersection between the epipolar line in the second image plane of the second imager with a projected target trajectory that is projected onto the second image plane of the second imager based on the target movement model; and
      determining the 3D position of the target based on the at least one intersection between the epipolar line in the second image plane of the second imager with the projected target trajectory.

2. The data processing method of claim 1 for updating a correlation model correlating a surrogate signal with the 3D position of the target, the update being based on an update signal being the 2D target position signal, and including the determined 3D position information of the target and the target movement model, further comprising:
   d) acquiring the surrogate signal; and
   e) correlating the surrogate signal with the determined 3D position of the target to obtain the updated correlation model.

3. The data processing method of claim 1, wherein the first imager is a single imager of a stereoscopic imaging apparatus.

4. The data processing method of claim 2, wherein the target movement model acquired in step a) is acquired based on at least one of:
   latest target detection on an obstructed or not used imager of the first imager and the second imager;
   latest stereoscopic target detection;
   latest prediction of the 3D position of the target, the prediction being based on the updated correlation model and the surrogate signal;
   latest prediction of the 3D position of the target being projected onto the respective imaging plane of an obstructed or not used imager of the first imager and the second imager.

5. The data processing method of claim 1, wherein the specific movement phases are associated with a surrogate signal or relative marker positions.

6. The data processing method of claim 1, wherein information on the specific movement phases is used when determining the 3D position of the target.

7. The data processing method of claim 2, wherein the updated correlation model is based on a number of update points distributed over a movement cycle or breathing cycle or respiratory cycle of the target.

8. The data processing method of claim 2, further comprising updating a prediction model predicting the 3D position of the target in a body using the updated correlation model.

9. The data processing method of claim 2, further comprising updating a prediction model predicting the 3D position of the target in a body, wherein the prediction model is updated based on the updated correlation model,
   wherein a prediction of the 3D position of the target in the body is made by:
   predicting a future value of the surrogate signal or a future position of a surrogate element using a surrogate movement model; and
   determining the predicted 3D position of the target in the body based on the predicted future value of the surrogate signal or the predicted future position of the surrogate element, using the updated correlation model.

10. The data processing method of claim 1, wherein the target movement model is stored in a memory and can be read from the memory.

11. The data processing method of claim 1, wherein the 2D target position signal is acquired by the first imager during a condition that the second imager has an obstructed line of sight to the target.

12. A data processing method performed by a computer for determining a three-dimensional (3D) position of a target, comprising:
   a) acquiring, using a first imager having a first imaging plane and a second imager having a second imaging plane, a target movement model specifying a movement cycle of the target, wherein the target movement model specifies at least two sections that are associated with an inhale phase and an exhale phase, and wherein the first imager and the second imager are respective imagers of a stereoscopic X-ray imaging apparatus;
   b) acquiring, using the first imager, a two-dimensional (2D) target position signal representing a view of the target in the first imaging plane of the first imager;
   c) determining the 3D position of the target based on the 2D target position signal acquired using the first imager and the target movement model,
      wherein the determining the 3D position of the target comprises:
      determining, based on the 2D target position signal, an epipolar line in the second image plane of the second imager corresponding to the view of the target in the first imaging plane of the first imager;
      determining at least one intersection between the epipolar line in the second image plane of the second imager with a projected target trajectory that is projected onto the second image plane of the second imager based on the target movement model; and
      determining the 3D position of the target based on the at least one intersection between the epipolar line in the second image plane of the second imager with the projected target trajectory.

13. The data processing method of claim 12 for updating a correlation model correlating a surrogate signal with a positional information of the target, the update being based on an update signal being the 2D target position signal and including the determined 3D position of the target and the target movement model, further comprising:
   d) acquiring the surrogate signal; and
   e) correlating the surrogate signal with the determined 3D position of the target to obtain the updated correlation model.

14. The data processing method of claim 12, wherein the 2D target position signal is acquired by the first imager during a condition that the second imager has an obstructed line of sight to the target.

15. A system for determining a three-dimensional (3D) position of a target comprising:
   a target movement model generator configured to acquire, using a first imager having a first imaging plane and a second imager having a second imaging plane, a target movement model specifying a movement cycle of the target, wherein the target movement model specifies at least two sections that are associated with an inhale phase and an exhale phase;
   a target position acquiring element configured to acquire, using the first imager, a two-dimensional (2D) target position signal representing a view of the target in the first imaging plane of the first imager; and
   a determination section connected to the target movement model generator and the target position acquiring element and receiving information or signals therefrom to determine, the 3D position of the target based on the 2D target position signal acquired using the first imager, and the target movement model,
   wherein the determination section is configured to:
      determine, based on the target position signal, an epipolar line in the second image plane of the second imager corresponding to the view of the target in the first imaging plane of the first imager;
      determine at least one intersection between the epipolar line in the second image plane of the second imager with a projected target trajectory that is projected onto the second image plane of the second imager based on the target movement model; and
      determine the 3D position of the target based on the at least one intersection between the epipolar line in the second image plane of the second imager with the projected target trajectory.

16. The system of claim 15 for updating a correlation model correlating a surrogate signal with a positional information of the target, the update being based on an update signal being the 2D target position signal and including the determined 3D position of the target and the target movement model, the system being further configured to:
   acquire the surrogate signal; and
   correlate the surrogate signal with the determined 3D position of the target to obtain the updated correlation model.

17. The system of claim 15, wherein the first imager is a single imager of a stereoscopic imaging apparatus.

18. The system of claim 16, wherein the updated correlation model is based on a number of update points distributed over a movement cycle or breathing cycle or respiratory cycle of the target.

19. The system of claim 15, wherein the target position acquiring element is configured to acquire the 2D target position signal by the first imager in a condition that the second imager has an obstructed line of sight to the target.

* * * * *